United States Patent [19]

Ilsink

[11] Patent Number: Plant 7,415

[45] Date of Patent: Jan. 8, 1991

[54] MINIATURE ROSE PLANT NAMED INTERELF

[75] Inventor: G. P. Ilsink, Leersum, Netherlands

[73] Assignee: Interplant B.V., Leersum, Netherlands

[21] Appl. No.: 392,567

[22] Filed: Aug. 11, 1989

[51] Int. Cl.[5] ..... A01H 5/00

[52] U.S. Cl. ..... Plt./9

[58] Field of Search ..... Plt./9

*Primary Examiner*—James R. Feyrer

*Attorney, Agent, or Firm*—Christie, Parker & Hale

[57] ABSTRACT

A new variety of miniature rose having light pink flowers produced on a good pot forcing plant.

2 Drawing Sheets

SUMMARY OF THE INVENTION

The present invention relates to a new and distinct variety of rose plant of the miniature rose class, which was originated by me by using as seed and pollen parents two unnamed, unpatented seedlings of my creation. The varietal denomination of the new variety is "Interelf".

Among the novel characteristics possessed by this new variety which distinguish it from its parent and all other varieties of which I am aware are its attractive pink flowers borne on a plant suitable for production of flowering pot plants. "Interelf" can be reproduced through propagation by cuttings or by grafting. Flowers of the new variety are long lasting on the plant. Asexual reproduction by budding and propagation by cuttings of the new variety as performed in Hazerswoude, Holland, shows that the foregoing and other distinguishing characteristics come true to form and are established and transmitted through succeeding propagation.

The accompanying drawings show typical specimens of the vegetative growth and flowers of the new variety in different stages of development and depicted in color as nearly true as it is reasonably possible to make the same in a color illustration of this character.

BRIEF DESCRIPTION OF THE DRAWINGS

FIG. 1 is an illustration of a plant of the new variety of miniature rose showing flowering and growth habit, however, the flower coloring shown is deeper than true; and, FIG. 2 is an illustration showing details of the new miniature rose variety and with more accurate flower coloring.

DESCRIPTION OF PREFERRED EMBODIMENT

The following is a detailed description of my new variety, with color terminology in accordance with the Royal Horticultural Society Colour Chart (RHSCC) and horitcultural terminology in accordance with standard terminology used in UPOV-approved horticultural guidelines. The terminology used in color description herein refers to plate numbers in the aforementioned color chart.

Parentage: Seedling.

*Seed parent.*—Unnamed seedling.

*Pollen parent.*—Unnamed seedling.

Class: Miniature.

As can be seen in the accompanying illustrations, FIG. 1 shows one sample of flowering plant "Interelf" depicting the pot plant habit of growth and flowering. Since flowering is nearly continuous, the floriferous "Interelf" pot plant can remain attractively in bloom for long periods when given proper care and culture.

FIG. 2 shows details of the new variety "Interelf". In the illustration there is shown the top of a young shoot, 1; compound three, five and seven leaflet leaves, 2, 3, and 4, respectively; a flower stem, 5; flower buds, 6, after sepals begin to separate, and 7, after petals begin to unfurl; a flower, 8, about one-half open, and a bloom, 9, fully open. Also shown are flower stems 10, 11 and 12, with reproductive organs but without petals.

The following further horticultural observations were made of specimens grown outdoor in Holland.

FLOWER

Blooming habit: Nearly continuous.

A. Bud:

(1) *Size.*—Medium.

(2) *Form.*—Pointed, ovate.

(3) *Color.*—As sepals divide, bud color is near 50D to 51D.

(4) *Sepals.*—Longer than bud, simple.

(5) *Peduncle.*—Length — about 3 to 3.5 cm. Aspect — straight. Strength — erect. Color — medium green.

B. Bloom:

*Flower.*—Average size for miniature; viewed from above — round; viewed from side: (A) upper part of fully opened flower — flattened convex; (B) lower part of fully opened flower — flat.

(1) *Size.*—Average size when fully expanded — about 3.5 to 4 cm.

(2) *Borne.*—Singly, one to a stem, and in small clusters.

(3) *Form.*—Ovoid at first, becoming flat then convex at maturity, outer petals reflex to points and inner petals roll under.

(4) *Petalage.*—Number of petals under normal conditions — about 24 to 32, fully double.

(5) *Color.*—After sepals fall and petals unfurl, predominant flower color viewing petals' top surface is light pink near 50D to 51C, D with deeper hues where petals bunch. Color is substantially stable and with some lightening of margins of outer petals. As blooms mature, flower coloring tends to lighten to near 55C to D. On reverse, petals are lighter toned, also near 55C to D. Petal color toward point of petal attachment is near 4D. Overall tonality from a distance is an attractive light pink.

(6) *Flowering.*—Medium number of flowers.

(7) *Flower pedicel.*—Medium hairs or prickles.

C. Petals:

(1) *Texture.*—Medium to thick.

(2) *Appearance.*—Inside velvety and outside satiny.

(3) *Form and size.*—Obovate shape, weak undulation at margin.

(4) *Arrangement.*—Regularly arranged, imbricated.

(5) *Petaloids in center.*—Ordinary.

(6) *Persistence.*—Drop off cleanly.

(7) *Fragrance.*—Slight to none.

(8) *Lasting quality.*—Long lasting quality on plant.

REPRODUCTIVE ORGANS

A. Stamens, filaments and anthers:

*Arrangement and color.*—Regularly arranged around styles; color — filaments light yellow.

B. Pollen:

*Color.*—Yellow.

C. Styles: Even, short bunched, little or no hairiness in upper half, light red.

D. Stigma: Full, orange red, about same level with anthers.

E. Hips: Small, pitcher-shaped.

PLANT

A. Form: Bushy.

B. Growth: Vigorous.

*Height attained.*—About 20 to 30 cm.

C. Foliage: Compound 3, 5 and 7 leaflets.

(1) *Size.*—Medium for a miniature.

(2) *Quantity.*—Abundant.

(3) *Color.*—Foliage at time of first flowering — dark green.

(4) *Shape.*—Oval, pointed.

(5) *Texture.*—Upper side is weakly glossy; under side is matte.

(6) *Edge.*—Serrate.

(7) *Serration.*—Ordinary, acuminate apices.

(8) *Leaf stem.*—Color — medium green.

(9) *Stipules.*—Medium length, light to medium green, distinct auricle.

(10) *Leaflet.*—Cross section — flat; terminal leaflet — length of blade, short to very short; maximum width narrow; shape of base, rounded; little or no undulation at margin; petiole length — short.

D. Wood:

(1) *New wood.*—Color — light green.

(2) *Old wood.*—Color — medium green.

E. Prickles (thorns):

(1) *Prickles.*—Substantially absent. On pedicel — very few.

F. Winter hardiness: Needs protection outdoors in severe climates.

I claim:

1. A new and distinct variety of rose plant of the miniature rose class, substantially as shown and described, characterized particularly by a plant suitable for growing in pots and by attractive light pink flowers which are long lasting on the plant.

* * * * *

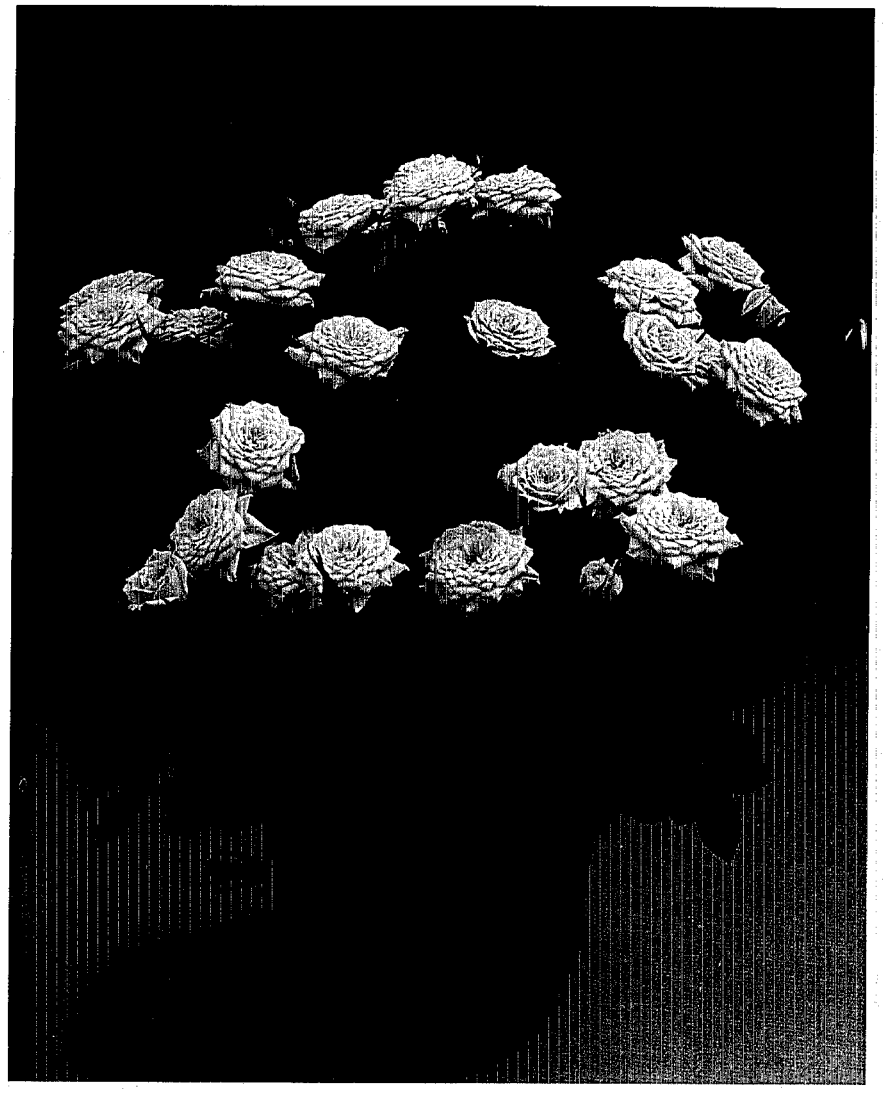

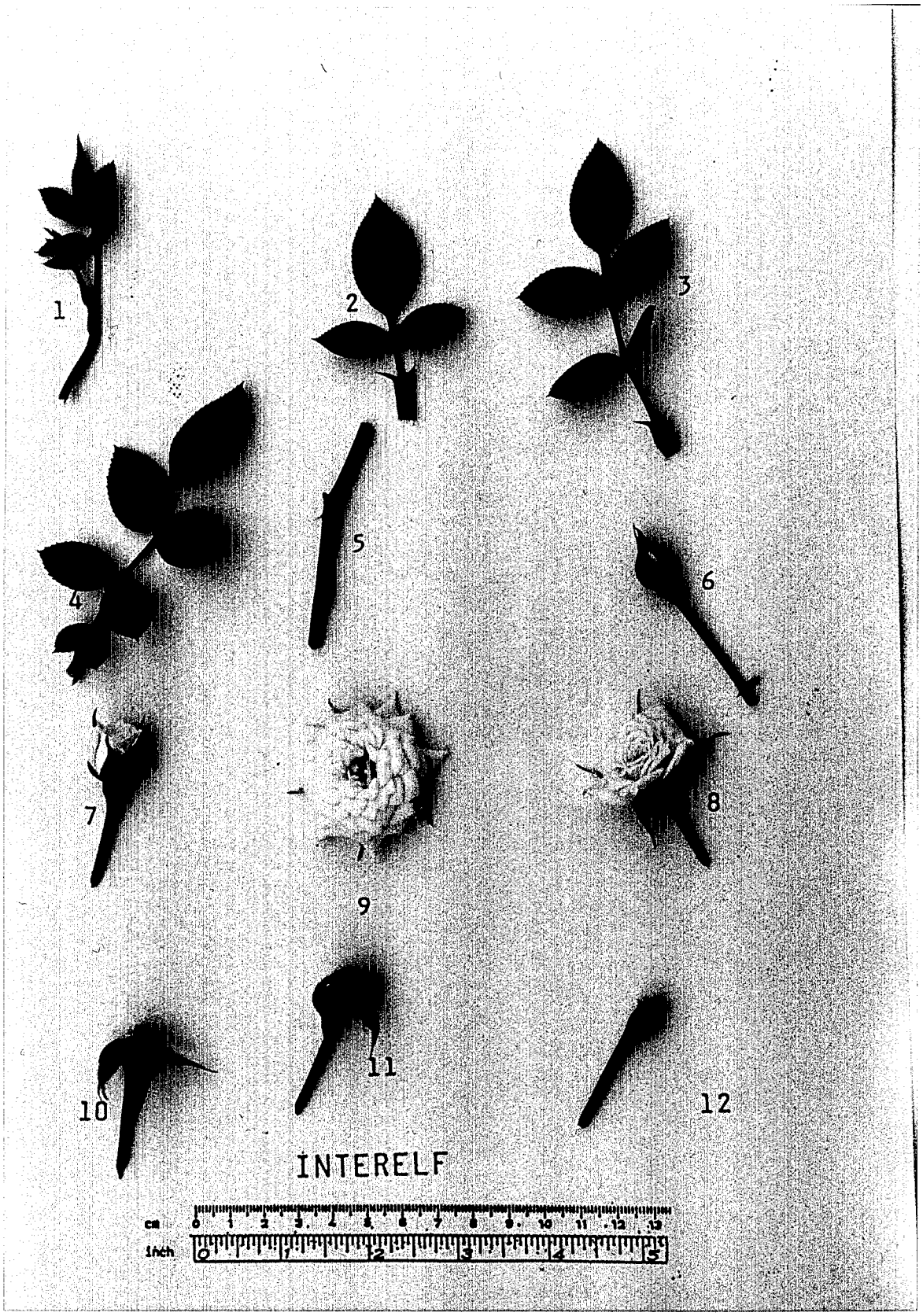
1
2
3
4
5
6
7
8
9
10
11
12
INTERELF
cm
inch